(12) United States Patent
Glover

(10) Patent No.: US 8,077,315 B2
(45) Date of Patent: Dec. 13, 2011

(54) MULTIPLE PATH LENGTH TRANSMITTANCE MEASURING DEVICE

(75) Inventor: James Andrew Glover, Whitby (CA)

(73) Assignee: 002134761 Ontario Ltd., Whitby, ON (CA)

( * ) Notice: Subject to any disclaimer, the term of this patent is extended or adjusted under 35 U.S.C. 154(b) by 358 days.

(21) Appl. No.: 12/309,079

(22) PCT Filed: Jul. 6, 2007

(86) PCT No.: PCT/CA2007/001281
§ 371 (c)(1),
(2), (4) Date: Jun. 16, 2009

(87) PCT Pub. No.: WO2008/003182
PCT Pub. Date: Jan. 10, 2008

(65) Prior Publication Data
US 2010/0007888 A1 Jan. 14, 2010

Related U.S. Application Data

(60) Provisional application No. 60/818,968, filed on Jul. 7, 2006.

(51) Int. Cl.
*G01N 21/00* (2006.01)
(52) U.S. Cl. .......................... 356/436; 356/440; 356/442
(58) Field of Classification Search .................. 356/436, 356/440–442
See application file for complete search history.

(56) References Cited

U.S. PATENT DOCUMENTS

| 3,553,454 A | 1/1971 | Olson et al. |
| 3,579,105 A | 5/1971 | Scott |
| 3,591,801 A | 7/1971 | Watson |
| 4,011,451 A | 3/1977 | Nelson |
| 4,021,670 A | 5/1977 | Noakes |
| 4,029,958 A | 6/1977 | Wright |
| 4,276,475 A | 6/1981 | Nelson |
| 4,577,106 A | 3/1986 | Fukasawa et al. |
| 4,775,794 A | 10/1988 | Behmann |
| 4,832,491 A | 5/1989 | Sharpe et al. |
| 5,021,196 A | 6/1991 | Crano et al. |
| 5,712,703 A | 1/1998 | Ando et al. |
| 6,365,906 B1 | 4/2002 | Spangenberg et al. |
| 6,818,900 B2 | 11/2004 | Ellis et al. |
| 2002/0066874 A1 | 6/2002 | Drescher |

*Primary Examiner* — Tarifur Chowdhury
*Assistant Examiner* — Tara S Pajoohi
(74) *Attorney, Agent, or Firm* — Lynn C. Schumacher; Hill & Schumacher

(57) ABSTRACT

A device to measure the amount of light able to transmit through a test liquid sample. A single lamp is used to illuminate a liquid sample cell containing the test water. A light detector is fixed relative to the lamp and is used to detect the amount of light from the lamp able to transmit through the liquid sample cell. The liquid sample cell is shaped in such a way as to provide at least two sets of opposed side walls that are able to transmit the light emitted from the lamp, where each set of opposed side walls defines a different path length through the liquid sample in the liquid sample cell. A rotation mechanism is used to provide relative rotation between the liquid sample cell and the lamp/light detector assembly. A microprocessor connected to the light detector calculates the light transmitted through at least two different path lengths through the liquid sample. Using these calculated transmittances the microprocessor then calculates the overall transmittance of the test water.

23 Claims, 2 Drawing Sheets

MULTIPLE PATH LENGTH TRANSMITTANCE MEASURING DEVICE

CROSS REFERENCE TO RELATED U.S PATENT APPLICATIONS

This patent application is a National Phase application claiming the benefit of PCT/CA2007/001281 filed on Jul. 6, 2007, which further claims the priority benefit from U.S. provisional patent application Ser. No. 60/818,968 filed on Jul. 7, 2006 entitled MULTIPLE PATH LENGTH TRANSMITTANCE MEASURING DEVICE, filed in English, which is incorporated herein in its entirety by reference.

FIELD OF THE INVENTION

The present invention is related to an apparatus for measuring water quality and particularly relates to several applications within the water and wastewater treatment industry.

BACKGROUND OF THE INVENTION

Rapid and reliable measurement of water quality is of major importance, particularly with respect to drinking water. Ultraviolet transmittance (UVT) is a water quality parameter that provides a measure of the amount of ultraviolet (UV) light able to transmit through a water sample. The ultraviolet absorbance (UVA) is a different representation of the measurement of UVT. UVA is mathematically related to UVT by the inverse log.

The ultraviolet transmittance (UVT) of a water sample under test (test sample) is a measure of the transmittance of water to UV light. Fundamentally, this requires a UV light source to shine UV light through a test sample and into a UV detector. However, to properly calculate the UVT of a test sample, the amount of UV light that is able to pass through the test sample must be compared to a reference of some kind. The reference is generally a sample of pure water which is said to have a UVT of 100% (blank sample), but any form of reference having known UVT could be used. By comparing the amount of UV light able to pass through the test sample to the amount of UV light able to pass through the blank sample, a useful value of UVT can be calculated for the test sample as a fraction or percentage. From the value of UVT, the UVA may then be calculated. There are many different UVT/UVA measuring devices available today that are able to measure the UVT/UVA of a test sample as compared to a blank sample using many different technologies and configurations.

There are two main types of UVT/UVA measuring devices. The first type is considered to be portable, although it may be permanently mounted as a benchtop instrument. It is designed to be operated by a user taking the UVT/UVA of grab samples and is typically used in water or chemical analysis labs or as a water or chemical analysis tool in the field. The second type is considered to be online such that it is directly connected to an incoming water source and continuously calculates the UVT/UVA of the incoming water. It is typically found in municipal water and wastewater treatment plants and industrial process water applications.

There are two main challenges when designing UVT/UVA instrumentation. The first challenge is due to the nature of UV light sources. The most common UV light source is the mercury lamp, which has a tendency to drift and fluctuate causing significant errors in the UVT/UVA measurements. Such fluctuation and drift is very common in UV lamps and is due primarily to changes in temperature and imperfections in the ballast and lamp, as well as the age of the lamp. Another major difficulty when designing UVT/UVA instrumentation is due to fouling of the optical path by various types of matter in the water. Dirt, oil and minerals can be deposited by the test water on optical windows and even on the UV detector and lamp. This deposition can significantly impair the UV light's ability to transmit to the sensor thereby causing significant errors.

For the above reasons it is necessary to recalibrate the UVT/UVA measuring device as frequently as possible in an attempt to reduce these errors.

The use of a blank sample for calibration, while potentially effective, causes various problems for both portable and online UVT/UVA measuring devices. For portable devices, the use of a blank sample typically requires filling a sample vial with the blank sample and performing a calibration procedure with the device followed by filling the sample vial with the test sample and performing a test procedure with the device. While the use of a blank sample as a reference for UVT/UVA calculations is acceptable in the lab it is not desirable in the field. Carrying blank samples in the field can be cumbersome and can cause problems in harsh climates where temperature and freezing can affect the UVT/UVA of the blank sample.

For online UVT/UVA measuring devices, the use of a blank sample is especially problematic since these devices generally require a constant flow of test water through the flow cell through which the UVT/UVA is measured. Typically, in order to calibrate a conventional online device the flow cell must be disconnected from the incoming test water, the flow cell must then be emptied of test water and replaced with water from a blank sample, then the calibration procedure must be performed, then the blank sample water must be removed from the flow cell and the incoming test water must then be reconnected to the flow cell. Clearly this is a time consuming process and prone to human error if performed by an operator. Some devices attempt to automate this process, however this requires additional fluid handling apparatus which makes the device both more expensive and bulkier.

Even if online UVT/UVA measuring devices do use an automatic blank sample calibration apparatus, the frequency that it is practically possible to calibrate is often only a few times per day at most, which is not nearly enough to prevent errors due to lamp fluctuations Newer designs have recently been introduced that allow the calculation of the UVT/UVA of test water without the need for blank samples, which is a significant improvement. The newer designs use a method of calculating the UVT/UVA by measuring the transmittance of light through different path lengths of the test water. By measuring the transmittance through at least two different path lengths of test water it is possible to compute the UVT/UVA of the test water while calibrating at the same time. The calculations required to determine the UVT/UVA using different path lengths depend on the number of path lengths used and what the path lengths are.

There are many different ways to design a device that measures UVT/UVA using multiple path lengths. The primary challenges all relate to difficulty implementing the different path lengths.

Several different approaches have been taken in the past. Some devices use a single UV detector and lamp, and by changing the relative position of the UV detector and lamp, two or more different path lengths may be defined. U.S. Pat. No. 6,818,900 describes such a device. However, there are several problems with this design. It is extremely important that the path lengths used are always consistent. This requires the positioning mechanism that defines the different path lengths to be highly accurate which adds to the cost of the device. Also, since the path lengths must be precisely known, this design also requires some form of path length factory calibration procedure which again adds to the cost of producing such a device. Also, this design requires that the test water chamber must contain moving parts. This requires water tight seals to be used which adds to the expense and also the maintenance of the device.

Other multiple path length designs require the use of multiple UV detectors. By simply fixing each UV detector a certain known distance from the lamp each UV detector is able to define a different path length. This allows the device to be designed with no moving parts. U.S. Pat. No. 6,791,092 describes such a device. However, this method introduces new errors due to the use of multiple sensors. Manufacturing is very costly since the relative distance between the lamp and each sensor must be very precise. Differences in the optics of each UV detector location can produce non-linear differences between the measurements made using each sensor. Differences in the electronic signal path of each UV detector can also significantly affect the measurements of each detector. Also, if each detector is looking at a different part of the lamp and/or looking at the lamp from a different angle, errors can occur since the UV lamp output varies not only over time, but also over the surface of the lamp. Therefore, using multiple UV detectors can reduce the effectiveness of the fundamental multiple path length concept.

Therefore, there is a need for a UVT/UVA measuring device which utilizes a multiple path length design while avoiding the aforementioned limitations.

SUMMARY OF INVENTION

Embodiments of the apparatus disclosed herein efficiently and accurately measure and compute the UVT/UVA of a test water source.

Embodiments disclosed herein uses a multiple path length design to measure the UVT/UVA of a test water source while compensating for lamp drift and fluctuations and for evenly distributed fouling of the optical path using only one sensor, and without the need for calibration to a blank sample.

Since natural organic matter (NOM) in water has strong absorption properties to UV light, the invention has many applications in the water and wastewater industry which require the measurement of NOM. Such applications include filtration, coagulation, chlorination, ozone and ion exchange treatment methods, as well as water and wastewater treatment plant efficiency and effectiveness.

Embodiments of the device disclosed herein can also help predict the potential formation of disinfection by-products (DBP's) formed by the reaction of chlorine and dissolved organics within a water or wastewater treatment system. This relates to the determination of the Specific UV Absorbance (SUVA) of a water sample, designated by the Environmental Protection Agency (EPA) as an important water quality parameter.

A single lamp is used to illuminate a liquid sample cell containing the test water. A light detector is fixed relative to the lamp and is used to detect the amount of light from the lamp able to transmit through the liquid sample cell. The liquid sample cell is shaped in such a way as to provide at least two sets of opposed side walls that are able to transmit the light emitted from the lamp, where each set of opposed side walls defines a different path length through the liquid sample in the liquid sample cell. A rotation mechanism is used to provide relative rotation between the liquid sample cell and the lamp/light detector assembly. A microprocessor connected to the light detector calculates the light transmitted through at least two different path lengths through the liquid sample. Using these calculated transmittances the microprocessor then calculates the overall transmittance of the test water.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which.

DETAILED DESCRIPTION OF THE PREFERRED EMBODIMENT

Generally speaking, the systems described herein are directed to an apparatus for measuring the transmittance of liquid samples to light using a multiple path length technique incorporating a moving measurement system. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an apparatus for measuring the transmittance of liquid samples to light using a multiple path length technique incorporating a moving measurement system.

As used herein, the term "about", when used in conjunction with ranges of dimensions, angles or other physical properties or characteristics, is meant to cover slight variations that may exist in the upper and lower limits of the ranges as to not exclude embodiments with concentrations slightly above or below those recited herein. It is not the intention to exclude embodiments such as these from the present invention.

The following description of the invention uses a UV light source and a UV light detector with the specific view of providing UVT/UVA measurements to allow the measurement of organics in test water. However, it should be clear to someone trained in the art that if desired the UV light source and the UV light detector can be replaced with a radiation source and detector combination that emits and detects any desired wavelength or combination of wavelengths.

Figure 1:
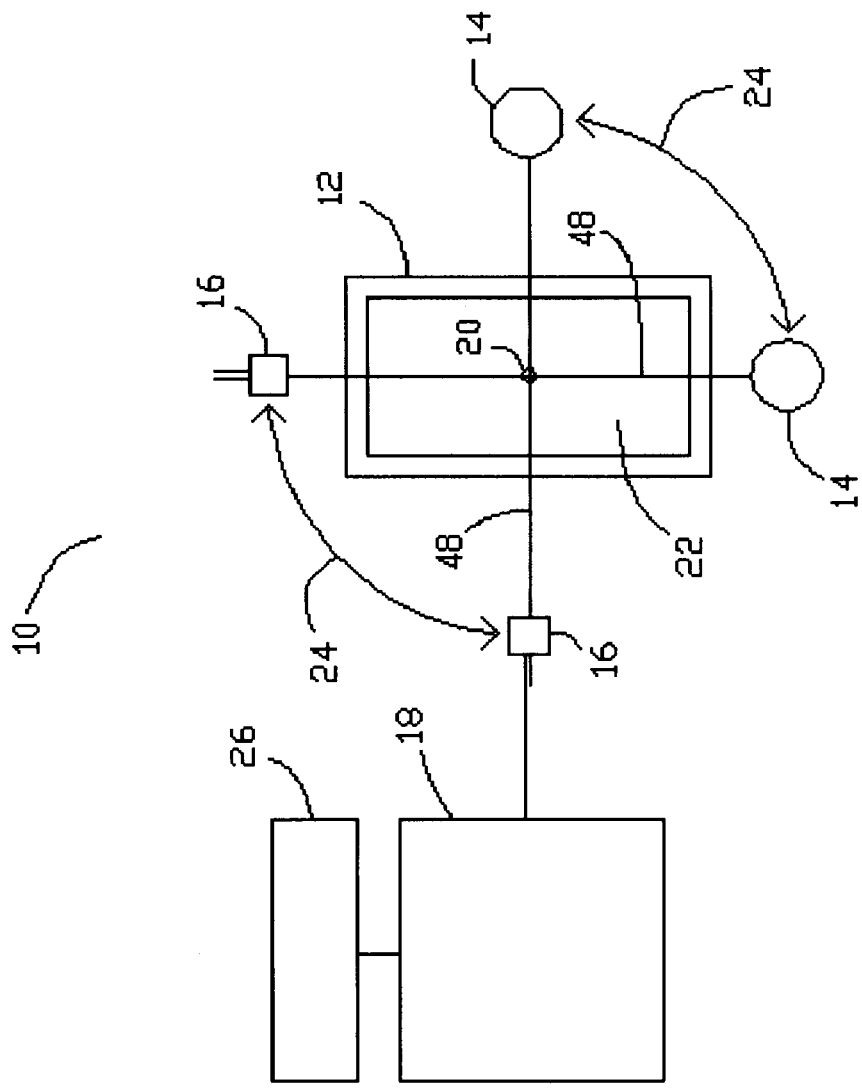
FIG. 1 is a block diagram showing a UVT/UVA measuring device constructed in accordance with a preferred embodiment of the present invention.

Referring to FIG. 1, a UVT/UVA measuring device constructed in accordance with the preferred embodiment of the present invention is shown generally at 10.

A flow cell 12 is used to hold the liquid sample being tested (test water 22) and/or allow the test water 22 to pass through the flow cell 12 at a predetermined flow rate. The flow cell 12 is made from a material that is transparent to UV light such as quartz. The flow cell 12 is preferred to be a rectangular prism and have a first inside width of 10 mm and a second inside width of 20 mm, however any size and shape of flow cell can be used provided it defines at least two different inside widths.

A flow cell with larger inside widths means the light must pass through more liquid and a flow cell with smaller inside widths means the light must pass through less liquid. Larger inside widths can improve performance at higher UVT values yet decrease performance at lower UVT values. Smaller inside widths can improve performance at lower UVT values yet decrease performance at higher UVT values. Regardless of the inside widths, the final UVT/UVA value may be determined relative to any desired path length. In the preferred embodiment, the final UVT/UVA value displayed is relative to a 10 mm path through the sample liquid. This is preferred since the industry accepted UVT/UVA parameter assumes a 10 mm path length. It is possible to use a flow cell with more than two different inside widths. For example, a skewed hexagonal prism flow cell could be used to provide three inside widths. Although additional inside widths does allow for additional accuracy verifications to be made, only two inside widths are necessary for the UVT/UVA to be calculated. The remainder of the detailed description assumes a flow cell 12 that provides two different inside widths.

It will be appreciated by those skilled in the art that the flow cell could be replaced by a single liquid sample cell. The single sample cell may have the same dimensions as the flow cell 12 discussed above, however, the single sample cell would be closed at the bottom to allow filling with a single sample of test water 22, whereas the flow cell 12 discussed above may or may not be closed at the bottom. The purpose of the single sample cell is to allow UVT/UVA measurements to be taken of individual liquid grab samples rather than taking continuous UVT/UVA measurements of flowing test water 22.

The UV light must pass through the flow cell 12 on its way from the UV lamp 14 to the UV detector 16 which is located such that it detects any UV light transmitted through flow cell 12. The UV lamp 14 and the UV detector 16 are fixed relative to each other via a UV lamp/UV detector fixture 48. Note that the UV lamp 14, UV detector 16 and UV lamp/UV detector fixture 48 appear twice in FIG. 1 even though the invention uses only a single UV lamp 14 and UV detector 16. The two instances of UV lamp 14, UV detector 16 and UV lamp/UV detector fixture 48 that appear in FIG. 1 are drawn to indicate the two measurement positions of the UV lamp 14 and UV detector 16, which are related to rotation mechanism 24.

Lamp 14 can be any UV light source that emits a wavelength that can be absorbed by organic matter, generally between 240-290 nm UV range. Lamp 14 can be a mercury lamp, deuterium lamp or a deep UV LED light source. In a preferred embodiment, lamp 14 may be a mercury low pressure UV lamp emitting radiation with a wavelength of 254 nm as the UV source.

In operation, the UV lamp 14 is allowed to reach a stable operating output characterized by a manageable amount of drift over time, as measured by the UV detector 16. Microprocessor 18 is programmed to determine when the output of UV lamp 14 has become stable enough by measuring and comparing the UV lamp output at predetermined time intervals. Once certain stability parameters are met, the microprocessor 18 then allows normal operation of the device to begin.

The UV light detector 16 may be sensitive to UV light in approximately the 200-400 nm range UV. UV detector 16 may be made of any conventional radiation sensor material sensitive to UV light in the 200-400 nm range UV. In a preferred embodiment UV light detector 16 is a common commercially available SiC UV photodiode.

The UV light detector 16 is mounted approximately halfway along the height of the flow cell 12 on a first side of the flow cell 12. The lamp 14 is mounted approximately halfway along the height of the flow cell 12 on a second side of the flow cell 12, such that the first side is opposite the second side. This arrangement defines a UV light path such that the UV light from the lamp 14 passes through the flow cell 12 before reaching the UV detector with a purpose of measuring the intensity of UV light transmitted through the flow cell 12.

The accuracy of UV detector readings, whether they measure the UV transmittance of the first flow cell width or the second flow cell width, can be improved by using signal conditioning electronics and/or by using various software averaging algorithms. In the preferred embodiment of the invention, both software averaging and signal conditioning electronics are used to improve UV detector reading accuracy. Such signal conditioning electronics can generally include trans-impedance amplifiers, signal gain amplifiers, and various common analog to digital converters (ADCs).

The UVT/UVA measurement requires the determination of the UV light transmitted through the flow cell 12 for both the first and second widths of the flow cell 12. This requires two separate UV transmittance measurements to be taken—one measurement must be taken for each flow cell 12 width. This fundamentally requires either the rotation of the flow cell 12 or the rotation of the lamp 14 and UV detector 16. The axis of rotation 20 may coincide with the imaginary line running along the centre of the rectangular prism formed by the flow cell 12, although it is not necessary. Rotating the flow cell 12 and rotating the lamp 14 and UV detector 16 are functionally equivalent for the purposes of the UVT/UVA calculation. The rotation may be automatic or may be performed manually by an operator, although for continuous online UVT/UVA measurement equipment, manual rotation is unlikely to be practical. Manual rotation is more applicable for portable field or lab equipment that would use a single sample cell in place of the flow cell 12. If a flow cell is used, automatic rotation of the flow cell 12 requires additional expense and maintenance due to the use of water tight gaskets. Therefore, for continuous online UVT/UVA measurement equipment, the preferred embodiment uses a rotation mechanism 24 to rotate the lamp 14 and UV detector 16 via the UV lamp/UV detector fixture 48, instead of rotating the flow cell 12.

It will be appreciated by those skilled in the art that if desired an implementation of the present invention may be configured to avoid the use of a rotation mechanism. However, such an implementation would require a much more complicated optical apparatus comprised of mirrors, beam splitters, and beam choppers and possibly even multiple sensors and/or lamps. The manufacturing expense and service related issues accompanying such designs would likely be more problematic than the relatively simple rotation mechanism given in the preferred embodiment.

The rotation mechanism 24 must be able to provide two lamp 14 and UV detector 16 measurement positions. The first measurement position allows a measurement by the UV detector 16 of the UV light transmitted from the lamp 14 through the first width of the flow cell 12. The second measurement position allows a measurement by the UV detector 16 of the UV light transmitted from the lamp 14 through the second width of the flow cell 12. Each measurement position must define the light path from the lamp 14 to the UV detector 16 to be approximately orthogonal to the flow cell 12. This can be accomplished by manually turning a single sample cell as discussed above. However, if a flow cell 12 is used the rotation will likely be accomplished by one of the two following fundamental automatic rotation mechanism implementations.

The first automatic rotation mechanism implementation requires the rotation mechanism 24 to continuously rotate in one direction about the flow cell 12. The rotation mechanism 24 can either stop at each measurement position or the measurements could be made while the rotation mechanism is rotating provided the measurements are made at each measurement position in a timely manner such that the rotation mechanism 24 does not rotate considerably during the time that each measurement is being taken. This rotation mechanism 24 can be a servo motor perhaps with positional feedback. Another method is to use a stepper motor which allows deterministic positioning of the motor shaft due to the fundamental stepping operation of the stepper motor. Yet another method is to use a simple DC motor to rotate the lamp 14 and UV detector 16 around the flow cell 12. This requires some form of electronic sensor such as IR LED/detectors or microswitches to detect the two measurement positions. Note that this automatic rotation mechanism implementation requires the rotation mechanism 24 to pass each of the two measurement positions twice during each full rotation of 360 degrees. Therefore, two full UVT/UVA measurements can be made during each full rotation.

The second automatic rotation mechanism implementation and the preferred embodiment of the invention requires that the rotation mechanism 24 rotate back and forth 90 degrees between the two measurement positions. This implementation is preferred since an inexpensive high-flex ribbon cable can be used to transfer signals and power to and from the rotation mechanism in contrast to the more expensive and less reliable rotary signal collar that is required for the first automatic rotation mechanism implementation. The back and forth rotation can be accomplished using a 90 degree servo motor perhaps with positional feedback. Another method is to use a stepper motor which allows deterministic positioning of the motor shaft due to the fundamental stepping operation of the stepper motor. The preferred embodiment uses a simple DC motor with mechanical stoppers to define the two measurement positions. Some form of electronic sensor such as IR LED/detectors or microswitches can also be used to detect the times that the lamp 14 and UV detector 16 reach the two measurement positions. In the preferred embodiment, the electronic sensor used is two microswitches which are referred to as first position detector (not shown) and second position detector (not shown) which detect the first and second measurement positions, respectively.

A microprocessor 18 is interfaced to the UV detector and the rotation mechanism 24. The microprocessor 18 is also interfaced to a visual display 26. Visual display 26 can be any type of display capable of indicating to the user the computed UVT/UVA of tested liquid samples, including LEDs, alphanumeric character LCDs and graphical LCDs. In the preferred embodiment visual display 26 is an alphanumeric character LCD.

The microprocessor 18 is also interfaced to an outbound communication mechanism to allow the device to be connected to a remote monitoring and/or control station.

As mentioned above, the UVT/UVA measurement procedure requires two transmittance readings to be taken. The first transmittance reading $T_a$ records the amount of UV light able to pass from the lamp 14 through a first flow cell width to the UV detector 16. The second transmittance reading $T_b$ records the amount of light able to pass from the lamp 14 through the second flow cell width to the UV detector 16, where the first flow cell width is smaller than the second flow cell width.

Note that the two transmittance readings are taken within a few seconds of each other. If the delay between transmittance readings $T_a$ and $T_b$ is too large, the UV lamp may have time to drift or fluctuate between the two transmittance readings which would introduce errors into the UVT/UVA calculation. Note that the order that the transmittance readings $T_a$ and $T_b$ are taken is not important. The preferred embodiment requires that transmittance reading $T_a$ is taken 500 ms from transmittance reading $T_b$, which requires a rotation mechanism 24 that uses a DC motor to have an angular velocity of 30 revolutions per minute.

Once the two transmittance readings $T_a$ and $T_b$ have been taken, software running on microprocessor 18 must use $T_a$ and $T_b$ along with the known first and second flow cell widths to determine the UVT/UVA of the liquid sample. The following equation illustrates how the UVT can be determined using two arbitrary flow cell widths, although this relationship could be represented in other forms including in terms of UVA:

$$UVT = \frac{T_b^{\frac{1}{b-a}}}{T_a^{\frac{1}{b-a}}} \cdot 100\% \qquad \text{E1}$$

where $T_a$ is the light transmitted through the shorter flow cell width, $T_b$ is the light transmitted through the longer flow cell width, a is the length of the shorter flow cell width, and b is the length of the longer flow cell width. Note the in equation E1, $T_a$ and $T_b$ are both raised to the exponent (1/b-a)

Since the preferred embodiment uses a flow cell with first and second widths of 1 cm and 2 cm respectively, equation E1 becomes:

$$UVT = \frac{T_b}{T_a} \cdot 100\% \qquad \text{E2}$$

where $T_a$ is the light transmitted through the shorter flow cell width and $T_b$ is the light transmitted through the longer flow cell width. Note that since the calculated UVT measurement of the preferred embodiment is relative to a 1 cm path length, the flow cell widths disappear from the equation. However, even equation E1 is simple enough to be easily calculated by microprocessor 18 if other path lengths are desired.

The result of equations E1 and E2 may need to be adjusted using a factory determined calibration curve or equivalent means to account for any offset errors or other errors introduced in the particular implementation of the design. Such errors would most likely be due to differences in the optical path due to the optics of the flow cell.

The UVA of the test sample is easily calculated from the UVT determined above using a simple calculation of the inverse log. The following equation provides the necessary calculation to convert UVT to UVA:

$$UVA = 2 - \log UVT \qquad \text{E3}$$

where UVT is calculated from equation E1 or E2 above.

UVT measuring device 10 may be configured to include a second UV detector to measure the output of lamp 14 directly without the light passing through the flow cell 12. The purpose of the second UV detector is to allow the microprocessor 18 to correct for changes in lamp output that occur between the times when the first UV detector 16 is detecting the amount of UV light transmitted through the first and second flow cell widths. Thus, the output from the second UV detector representing the intensity of the UV lamp 12 allows the device to automatically correct for any lamp fluctuations that occur during this short interval.

Fouling of the optical path by various types of matter in the water is very common in this type of instrumentation. Dirt, oil and minerals can be deposited by the test water on optical windows. This deposition can significantly impair the UV light's ability to transmit to the sensor thereby causing significant errors. A second UV detector intrinsically allows the determination of raw lamp output. This allows the microprocessor to be able to distinguish between overall fouling and lamp output drift. This means information can be provided to the operator about overall fouling of the optical path and therefore automatic indication can be given to the operator when manual cleaning of the flow cell 12 is required. If an automatic cleaning mechanism is used the indication of overall fouling could be used to trigger an automatic cleaning procedure. The second UV detector also allows the invention to automatically indicate to the operator when the lamp output is low and therefore when a lamp replacement is required which would otherwise be unable to be determined due to interference from fouling of the optical path.

Figure 2:
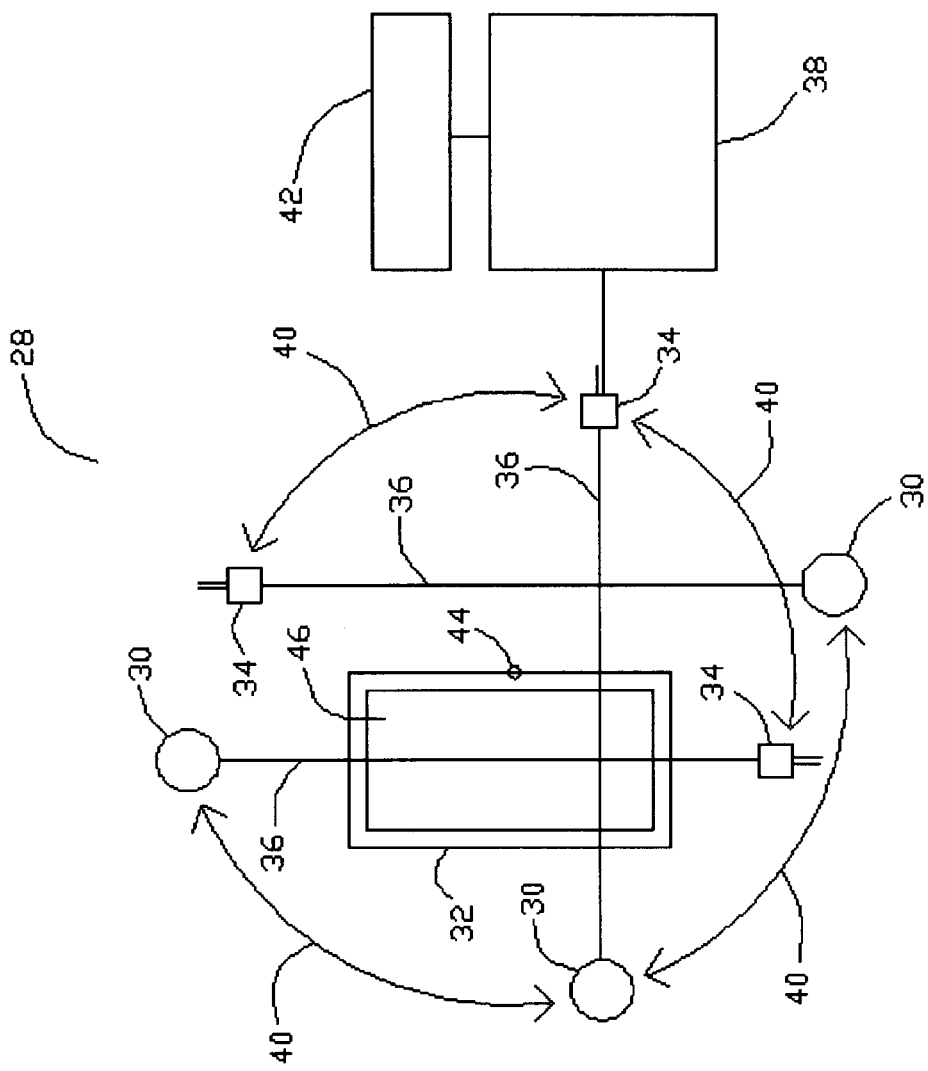
FIG. 2 is a block diagram showing a UVT/UVA measuring device constructed in accordance with a second embodiment of the present invention.

Raw lamp output can also be calculated without using an additional UV detector. Referring to FIG. 2, this requires a second embodiment of the invention 28 which incorporates all the same components and the same fundamental apparatus as the first embodiment. The fundamental difference between the preferred embodiment and the second embodiment is that in the second embodiment the axis of rotation 44 of the rotation mechanism 40 is not coincident with the imaginary line running along the centre of the rectangular prism formed by the sample cell 32 containing the test water 46. This intrinsically causes the radius of rotation to be larger in the second embodiment than in the preferred embodiment. Note that, as in the preferred embodiment of the invention, the purpose of the rotation mechanism 40 in the second embodiment is to provide relative rotation between the UV lamp/UV detector fixture 36 and the sample cell 32. In the second embodiment, this relative rotation allows the rotation mechanism 40 to define three measurement positions instead of only two measurement positions defined in the preferred embodiment. The third measurement position provides a direct light path from the lamp 30 to the UV detector 34. The first two UV detector readings are the transmittance readings at the first two measurement positions defined by the two flow cell widths, and the third UV detector reading is the raw lamp output with a clear path from the UV lamp 30 to the UV detector 34. Note that the UV lamp 30 and UV detector 34 appear three times in FIG. 2 even though the invention uses only a single UV lamp 30 and UV detector 34. The three instances of both the UV lamp 30 and the UV detector 34 that appear in FIG. 2 are drawn to indicate the three measurement positions of the UV lamp 30 and UV detector 34, which are related to rotation mechanism 40.

As in the preferred embodiment, the second embodiment incorporates a microprocessor 38 which is connected to the light detector 34 and is capable of calculating the light incident on the light detector 34 emitted from the lamp 30 and transmitted through the flow cell 32. The microprocessor 38 is also connected to the rotation mechanism 40 such that it can determine the times that the light is shining through a particular flow cell width. As with the first embodiment, the microprocessor 38 uses the calculated transmittances of each flow cell width to determine the overall transmittance of the test liquid 46 contained in the flow cell 32. A visual display 42 connected to the microprocessor 38 is used to display the calculated UVT/UVA Another way to reduce errors caused by changes in lamp output that occur between the times when the UV detector 16 is in the first and second measurement positions, is to use a software trending algorithm. Microprocessor 18 may use a software trending algorithm to allow the lamp output to be approximately predicted from previous readings from the UV detector 16, in an attempt to predict and therefore reduce any errors resulting from changes in lamp output that occur during this short interval.

The apparatus disclosed herein may have an additional light detector (not shown) positioned at an angle such that it is able to substantially detect light that is scattered by material in the test water 22. Scattered light is due to material in the water that deflects light rather than absorbs it. This measurement of scattered light allows an industry accepted measure of turbidity to be calculated. The turbidity can be used as additional water quality information or simply to allow compensation to be made for turbidity causing material that may interfere with the measurement of absorbing material.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An apparatus for measuring the transmittance of a liquid sample to radiation, comprising:
    a lamp for emitting light;
    a light detector for detecting an intensity of light emitted by said lamp;
    a sample cell for holding a test liquid having at least two sets of opposed side walls where each set of opposed side walls defines a different cell width and is able to transmit the light emitted by the lamp;
    a lamp and light detector fixture incorporating said lamp and said light detector wherein said lamp is fixed relative to said light detector and spaced such that a light path between said lamp and said light detector is defined;
    a rotation mechanism to provide relative rotation between said sample cell and said lamp and light detector fixture such that the light path passes through at least two sets of said opposed side walls at different times;
    a microprocessor connected to said light detector, said microprocessor including processing means for processing light intensity signals received from said light detector, said microprocessor including processing means configured for
    i) calculating a light intensity of light transmitted through at least two sets of opposed side walls of said sample cell containing a test liquid; and
    ii) calculating a transmittance of the test liquid using the light intensities determined in (i) and the associated sample cell widths.

2. The apparatus according to claim 1 wherein said rotation mechanism defines an axis of rotation which coincides with the centre of said sample cell.

3. The apparatus according to claim 1 wherein said rotation mechanism defines an axis of rotation which does not coincide with the centre of said sample cell such that said light path passes through at least two sets of said opposed side walls at different times and such that the light path passes directly from said lamp to said detector at other times, and wherein said microprocessor is configured to calculate a level of overall fouling of the at least two sets of side walls over time and to calculate lamp performance over time.

4. The apparatus according to claim 1 wherein said sample cell holds one liquid sample at a time.

5. The apparatus according to claim 1 wherein said sample cell is a flow cell through which a liquid is continuously flowed.

6. The apparatus according to claim 1 wherein said microprocessor includes processing means for converting said transmittance of the liquid test sample to units of absorbance.

7. The apparatus according to claim 1 including a second light detector connected to said microprocessor positioned to receive light directly from said lamp, and wherein said microprocessor is configured to correct for changes in lamp output that occur between times when the transmittance of each set of opposed side walls is measured.

8. The apparatus according to claim 1 wherein the microprocessor includes one of a look-up-table and calibration curve to correlate said calculated transmittance of the test liquid to a transmittance value that has been factory adjusted to compensate for any offset errors or other errors introduced by various factors including imperfections in the optical layout of the apparatus.

9. The apparatus according to claim 1 wherein said microprocessor is configured with a software trending algorithm to allow lamp output to be approximately predicted from previous readings from the light detector.

10. The apparatus according to claim 1 including a display connected to said microprocessor for displaying the transmittance, absorbance, or both, of the test liquid as calculated by said microprocessor.

11. The apparatus according to claim 1 wherein said microprocessor is configured to calculate the lamp output to determine when the lamp output is stable and will no longer vary its output by more than a pre-defined percentage of the lamp output.

12. The apparatus according to claim 1 wherein said sample cell is made from a material that is substantially transparent to the light emitted by said lamp.

13. The apparatus according to claim 1 wherein said rotation mechanism is configured to rotate said sample cell to provide relative rotation between the sample cell and the lamp and light detector fixture.

14. The apparatus according to claim 1, wherein said rotation mechanism is configured to rotate said lamp and light detector fixture to provide relative rotation between the sample cell and the lamp and light detector fixture.

15. The apparatus according to claim 1 wherein said rotation mechanism is connected to said microprocessor and configured to provide rotation under control of said microprocessor.

16. The apparatus according to claim 1 wherein said rotation mechanism is configured to be manually rotated under control of an operator.

17. The apparatus according to claim 1 wherein said lamp is selected to emit light at a pre-selected wavelength and said light detector is configured to detect light at said pre-selected wavelength.

18. The apparatus according to claim 1 wherein said lamp emits light at more than one pre-selected wavelength of light and said light detector is configured to individually detect each pre-selected wavelength of light.

19. The apparatus according to claim 18 wherein said microprocessor is configured to use light measured by the light detector at one or more wavelengths to calculate the transmittance of the water in the sample cell at one or more wavelengths of light.

20. The apparatus according to claim 19 wherein said microprocessor is configured to use one or more of the wavelengths measured by the light detector to compensate for material present in the water in the sample cell that interferes with a desired measurement of a particular material in the water where different materials absorb and/or scatter light of different wavelengths by different amounts.

21. The apparatus according to claim 1 wherein said lamp is configured to emit a pre-selected spectrum of light and said light detector is configured to detect each of said pre-selected wavelengths of light.

22. The apparatus according to any one of claim 1 further including an additional light detector positioned to detect scattered light due to scattering by particulate material in the water.

23. The apparatus according to claim 22 wherein said microprocessor is configured to use the detected scattered light to determine a turbidity of the water in the sample cell.

* * * * *